(12) United States Patent
Lekare

(10) Patent No.: US 7,223,387 B2
(45) Date of Patent: May 29, 2007

(54) ANTIVIRAL FORMULATIONS COMPRISING PROPYLENE GLYCOL AND AN ISOPROPYL ALKANOIC ACID ESTER

(75) Inventor: Gunilla Lekare, Borlange (SE)

(73) Assignee: Medivir AB, Huddinge (SE)

( * ) Notice: Subject to any disclaimer, the term of this patent is extended or adjusted under 35 U.S.C. 154(b) by 477 days.

(21) Appl. No.: 10/334,487

(22) Filed: Dec. 30, 2002

(65) Prior Publication Data

US 2003/0171344 A1 Sep. 11, 2003

Related U.S. Application Data

(63) Continuation of application No. 09/831,981, filed on Jul. 24, 2001, now abandoned.

(30) Foreign Application Priority Data

Nov. 18, 1998 (SE) ................................ 9803929

(51) Int. Cl.
- A61K 31/74 (2006.01)
- A01N 43/90 (2006.01)
- A01N 45/00 (2006.01)
- A01N 43/00 (2006.01)

(52) U.S. Cl. .............. 424/78.07; 424/78.02; 514/171; 514/177; 514/262.1

(58) Field of Classification Search ............ 514/262.1, 514/171, 177; 424/78.02, 78.07
See application file for complete search history.

(56) References Cited

FOREIGN PATENT DOCUMENTS

| | | |
|---|---|---|
| EP | 0 044 543 A1 | 7/1981 |
| EP | 0 416 739 A1 | 8/1990 |
| WO | WO 91/11187 | 8/1991 |
| WO | WO 93/00905 | 1/1993 |
| WO | WO9624355 | 8/1996 |
| WO | WO9817316 | 4/1998 |

OTHER PUBLICATIONS

Block, Remington: The Science and Practice of Pharmacy, 1995, p. 1588.
Abstract "Failure of topical.." Freeman, DJ. et al.; Antimicrob Agents Chemother May 1986; 29.
Abstract "Acyclovir bioavailability.." Parry, GE. et al.; J Invest Dermatol Jun. 1992; 98 (6): 856-63.
Spruance, Spotswood L., "Herpes simplex labialis," Clinical Management of Herpes Viruses, 1995, pp. 3-42.
Spruance, Spotswood L. et al., "High-does, short duration, early valacyclovir . . . ," Antimicrobial Agents and Chemotherapy, Mar. 2003, p. 1072-1080.
Spruance, Spotswood L. et al., "Acyclovir cream for treatment of herpes simplex . . . ," Antimicrobial Agents and Chemotherapy, Jul. 2002, p. 2238-2243.
Spruance, Spotswood, L. et al., "Penciclovir cream for the treatment of herpes simplex . . . ," JAMA, May 7, 1997, vol. 277, No. 17, pp. 1374-1379.
Spruance, Spotswood, L. et al., "The natural history of recurrent herpes . . . ," The New England Journal of Medicine, vol. 297, No. 2, pp. 69-75.
Harmenberg, Johan G. et al., "ME-609: a treatment for recurrent herpes simplex . . . ," Antiviral Chemistry & Chemotherapy, 14(4), pp. 205-215.
Evans, T.G. et al., "Double-blind, randomized, placebo-controlled . . . ," Antimicrobial Agents and Chemotherapy, Jun. 202, p. 1870-1874.

Primary Examiner—San-Ming Hui
(74) Attorney, Agent, or Firm—Birch, Stewart, Kolasch & Birch, LLP (57) ABSTRACT

A topical composition comprising an antiinflammatory glucocorticoid and a nucleoside analogue antiviral agent in a pharmaceutical carrier characterized in that the carrier comprises about 15 to about 25 weight % propylene glycol and about 10 to about 25 weight percent isopropyl $C_{12}$–$C_{22}$ alkanoic ester. The compositions have utility in the treatment or prophylaxis of herpesvirus infections and exhibit superior antiviral and therapeutic efficacy and an improved shelf life.

20 Claims, 7 Drawing Sheets

ANTIVIRAL FORMULATIONS COMPRISING PROPYLENE GLYCOL AND AN ISOPROPYL ALKANOIC ACID ESTER

TECHNICAL FIELD

This invention relates to topical antiviral formulations suitable for orofaciial or genital application and comprising an antiinflammatory agent and an antiviral agent. The invention further relates to the treatment or prophylaxis of herpesvirus diseases using such formulations and to their preparation.

BACKGROUND ART

International patent application no WO 96/24355 decribes pharmaceutical compositions comprising a topically acceptable antiviral substance and an antiinflammatory glucocorticoid in a pharmaceutically acceptable carrier. The carriers disclosed in this application comprise conventional formulations for each of the respective active agents, that is a conventional antiviral formulation is combined with a conventional glucocorticoid formulation. Such combined formulations have a large number of ingredients, with potential for interreacting with each other, leading to unknown stability and physicochemical characteristics.

European patent application no. EP 44543 relates to oil in water formulations of the acyclic nucleoside antiviral agent acyclovir and describes that effective topical penetration necessitates that the carrier comprises at least 30 weight percent, preferably at least 40 weight percent propylene glycol. This formulation, denoted the MAC formulation, forms the basis of the most widely marketed topical acyclovir preparation.

International patent application no WO 91/11187 relates to oil in water or aqueous topical formulations of the acyclic nucleoside antiviral agent penciclovir. These formulations must comprise at least 30 weight percent, preferably at least 35 weight percent, propylene glycol. European patent application no. EP 416 739 relates to topical formulations of penciclovir comprising at least 30 weight percent propylene glycol and a decyl methyl sulfoxide emulsifier. International patent application no. WO 93/00905 relates to topical formulations of penciclovir comprising at least 30 weight percent, preferably at least 35 weight percent, propylene glycol and a cetomacrogol 1000 emulsifier.

Formulation of a combination product comprising a strongly lipophilic component such as hydrocortisone and a moderately lipophobic component such as an acyclic nucleoside analogue is difficult in the case of conventional pharmaceuticals, but is even more difficult in the case of a topical preparation where release rates of the active ingredients into the target tissue must be taken into account. As described in the publications in the two paragraphs immediately above, it has hitherto been regarded essential to utilise a high level of propylene glycol when formulating acyclic nucleosides in order to achieve adequate penetration of the antiviral agent into the skin or dermal mucosa. We have discovered, however, that while conventional, high concentration propylene glycol carriers can be used to prepare efficacious antiviral compositions within the scope of the above mentioned WO 96/24355 (that is compositions comprising a glucocorticoid and an antiviral agent), these conventional carriers result in the product having an undesirably short shelf life and less than optimal antiviral and therapeutic performance.

DISCLOSURE OF THE INVENTION

In accordance with the invention there is provided a topical composition comprising an antiinflammatory glucocorticoid and a nucleoside analogue antiviral agent in a pharmaceutical carrier characterized in that the carrier comprises about 15 to about 25 weight % propylene glycol and about 10 to about 25 weight % isopropyl $C_{12}$–$C_{22}$ alkanoic acid ester.

In the context of the invention, this combination of a lower concentration of propylene glycol in conjunction with an isopropyl alkanoic acid ester allows for good penetration and release of the antiviral component, while at the same time avoiding the instability shown by conventional antiviral compositions.

The compositions of the invention are useful for the treatment or prophylaxis of diseases caused by members of the herpesvirus family, such as herpes simplex type 1 (predominantly an orofacial infection), herpes simplex type 2 (predominantly a genitoanal infection), varicella zoster virus primary infection (chicken pox) and secondary infection (shingles), human herpesvirus type 6 and 8 (implicated in the skin condition Kaposi's sarcoma) and the like. Prophylaxis in the context of the invention includes prevention of infection (including preventing spread to adjacent healthy tissue) and preventing reactivation of previous herpes virus infection, such as reactivation of herpes lying dormant in neural tissue.

A further aspect of the invention thus provides the use of the composition defined above in medicine, particularly in the manufacture of a topical medicament for the treatment or prophylaxis of herpes virus infections in humans, especially herpes simplex type 1 and herpes simplex type 2. A related aspect of the invention provides a method for the treatment or prophylaxis of herpes virus infection in humans comprising the topical administration of the composition described above to a subject in need thereof.

Weight percentages herein refer to the weight of the component relative to the weight of the composition.

Preferred antiviral agents include ganciclovir, N-7 ganciclovir, bis-hydroxymethylcyclopropylmethylguanine, lobucovir, adefovir, cidofovir and the like. Particularly preferred antiviral agents include penciclovir, 9-[4-hydroxy-2-(hydroxymethyl)butyl]guanine (H2G) and especially acyclovir. The antiviral agent may be in the form of a prodrug which is metabolised in situ, for instances with epidermal esterases or xanthine oxidases, to form an antiviral agent such as the ones listed above.

The antiviral agent is included in the formulation in substantially conventional concentrations for the respective nucleoside, for example 0.5 to 15 weight percent, preferably 1–7 weight percent such as around 4–5 weight percent. Advantageously the formulation is largely or completely saturated with respect to the antiviral agent.

Examples of glucocorticoids include alclometasone, desonide, fluprednidene, flumethasone, hydrocortisone and its esters such as hydrocortisone butyrate or hydrocortisone acetate, clobetasone, triamcinolone acetonide, betmethasone, budenoside, desoximethasone, diflorosane, fluocinolone, fluoccinonide acetonide, fluocortolone, fluticasone, methylprednisolone aceponate, mometasone, rofleponide and the like. Mild glucocorticoids, such as those in Nordic class I, are preferred. Hydrocortisone and its esters are particularly preferred.

The glucocorticoid is included in the formulation in substantially conventional concentrations for the respective glucocorticoid, which concentrations are well known in the glucocorticoid art and generally fall in the range 0.005 to 12 weight percent, such as 0.1 to 10 weight percent. For instance when employing a mild (Nordic class I) glucocorticoid such as hydrocortisone, the formulation may contain 0.1 to 10 weight percent, preferably 0.5 to 2 weight percent, such as about 1 weight percent hydrocortisone.

The glucocorticoid and antiviral components may be in substantially dissolved form, dependent upon the carrier, but are conveniently prepared from a micronised raw material, such as those having >75%, preferably greater than 90% of particles with less than a defined particle size. For instance the glucocorticoid hydrocortisone is conveniently prepared from a raw material with a particle size less than 5 µm. The antiviral acyclovir or penciclovir is conveniently presented with a particle size less than 15 µm, preferably less than 7 µm.

In general the compositions of the invention are biphasic and comprise discrete oil and aqueous phases, either as an oil in water or a water in oil emulsion. Preferably the composition comprises a dispersed oil phase and a continuous aqueous phase. The isopropyl alkanoic acid ester and the typically lipophilic glucocorticoid component will be preferentially found in the oil phase, while the antiviral nucleoside will generally be found in the aqueous phase, typically in conjunction with the propylene glycol.

Components of the oil phase may include conventional fats and oils and their esters, as found in the European and other pharmacopeaias. Oil phase components are preferably non-greasy, non staining and washable. Conventional pharmaceutical oil phase components include mineral oils such as vaseline, liquid paraffin and the like, alkanoic acids such as stearic acid and fatty alcohols such as cetostearyl alcohol, straight or branched chain mono or dibasic alkyl esters such as di-isopropyl adipate, isocetyl stearate, propylene glycol diester of coconut fatty acids, decyl oleate, butyl stearate, 2-ethylhexyl palmitate and other 2-ethylhexanoic acid esters and the like.

Preferred isopropyl alkanoic acid esters include the dodecanate, myristate, palmitate, stearate, eicosanate or behenoate esters, especially isopropyl myristate. The composition of the invention comprises about 10 to about 25 weight percent of the isopropyl alkanoic acid ester, preferably about 12 to about 18 weight percent, such as about 15 weight percent.

The composition of the invention comprises about 15 to about 25 weight percent propylene glycol, such as around 18 to around 22 weight percent. Conveniently the propylene glycol content is around 20 weight percent as this concentration generally assures a good preservative effect without needing exogenous preservatives in the composition.

The composition of the invention conveniently includes an emulsifier (surfactant), typically in an amount of 0.05 to 5, preferably 0.1 to 1 weight percent. The European Pharmacopeia describes a number of pharmaceutically acceptable emulsifiers including anionic, cationic and non-ionic emulsifiers.

Exemplary non-ionic emulsifiers include cetomacrogols, such as cetomacrogol 1000, ethylene or diethylene glycol monostearate, glyceryl esters such as the behenate, oleate, stearate etc, laureth compounds such as lauromacrogols, macrogol monomethyl ethers, mono-and diglycerides, nonoxinols, octoxinols, poloxamers such as poloxamer 407, polyoxyl castor oils, polyoxyl stearates, polysorbates, polyvinyl alcohols, propylene glycol diacetates, sorbitan esters and the like. Poloxamer 188 is a preferred non-ionic surfactant.

Exemplary anionic emulsifiers include aluminium monostearate, calcium stearate, sulphated castor oil, magnesium stearate, pendecamaine, sodium oleate, sodium stearate, sodium stearyl fumarate, sodium tetradecyl sulphate, zinc stearate and the like. A preferred anionic emulsifier is sodium lauryl sulphate The compositions of the invention can also include conventional auxiliaries such as surface anaesthetics, sunscreens, flavours, scents, emollients or skin tone colourants and masks.

The compositions of the invention can be prepared by conventional blending techniques. Preferably the compositions are prepared by conventional biphasic blending techniques, whereby the oil and aqueous/propylene glycol phases are separately blended and homogenised and brought to a common temperature before mixing. The active ingredients (that is the glucocorticoid and the nucleoside analogue) may be added to their respective oil and aqueous phases before or after blending. Preferably, to minimize the tendency to recrystallisation, the active ingredients are added after blending of the two phases. This means that there is a greater volume when the active ingredients are added, and additionally the biphasic mixture is generally at a lower temperature.

A further aspect of the invention thus provides a method for the preparation of an antiviral composition comprising bringing an oil phase comprising 10–25 weight percent (relative to the total weight of the intended formulation) isopropyl alkanoic acid ester to a defined temperature, bringing an aqueous phase comprising 15–25 weight percent (relative to the total weight of the intended formulation) propylene glycol to the defined temperature, blending and optionally homogenising the two phases, optionally allowing the blend to cool to a lower temperature, adding effective amounts of an antiinflammatory glucocorticoid and a nucleoside analogue antiviral agent and homogenising the resultant blend.

The intended viral conditions, such as herpes simplex lesions on the lips and/or genitalia or herpes zoster (shingles), are episodic. As with all antiviral treatments it is desirable to commence application of the medicament as soon as possible after the reactivation of a dormant herpes infection into an incipient lesion is sensed or suspected. For instance many people experience a warmth or tingling at the coming focal point one or more days before the first visual signs of a herpes lesion become discernable. Application of the composition of the invention is preferably commenced at this point. In some patients, exposure to certain stimuli, such as UV light when skiing or from tropical sun, severe emotional stress or menstruation, can induce reactivation of herpes lesions in particular positions. The composition of the invention can be applied in a prophylactic manner upon exposure to these stimuli. In either event it will be convenient for people prone to herpes lesions to keep a supply of the composition readily available for speedy application when needed. Accordingly it is desirable for the composition of the invention to have a long shelf life without refrigeration, so that the medicament can be kept at home or at work and/or packed for travel.

The composition will generally be applied to the incipient or apparent lesion two to twelve times per day during an episode, such as every three hours. Application preferably continues at least until the hard scab stage which generally takes 3 to 10 days from the first sensation that an episode is expected.

The composition of the invention is preferably presented in a tube containing 0.25 to 50 ml. Conveniently the tube contains sufficient for a single cold or genital sore episode, such as 1 to 5 ml. This will allow several daily applications over no more than a week or ten days, the residue being discarded, thus minimizing potential contamination of the open tube and/or cross infection between individuals sharing the same tube.

Preclinical efficacy of compositions of the invention can be assayed as shown in the examples or with the adoptive transfer of immunity model described in WO 96/24355 and WO 96/24963

BRIEF DESCRIPTION OF THE DRAWINGS

Various embodiments of the invention will now be illustrated by way of example only with reference to the following non-limiting examples and drawings in which.

DETAILED DESCRIPTION

EXAMPLE 1

A composition in accordance with the invention is prepared from the following ingredients:

| oil phase | | |
|---|---|---|
| cetostearyl alcohol | 6.75 g | 6.75% |
| vaseline | 10.00 g | 10.0% |
| liquid paraffin | 5.65 g | 5.65% |
| isopropyl myristate | 15.00 g | 15.0% |
| aqueous phase | | |
| propylene glycol | 20.00 g | 20.0% |
| sodium lauryl sulphate | 0.80 g | 0.8% |
| poloxamer 188 | 1.00 g | 1.0% |
| aq. purif. | 34.8 g | 34.8% |
| active components | | |
| acyclovir | 5.00 g | 5.0% |
| hydrocortisone | 1.00 g | 1.0% |

The particle size of the acyclovir (Recordati micronised, USP23/BP93/Eur Ph III) was 10%=2 µm, 50%=4 µm, 90%=7 µm & 100%=15 µm. The particle size of the hydrocortisone (Pharmacia & Upjohn micronised USP/EP/BP) was 100% <5 µm, geometric mean diameter 2 µm. The purified water is reverse osmosis treated.

The oil phase and aqueous phase components are added to respective mixing vessels, which are each heated to 70° C. under agitation. When the phases are at an identical temperature, the oil phase is poured onto the aqueous phase from above while continuing to agitate for 3–5 minutes at the highest possible speed which avoids drawing air into the mixture. The thus emulsified mixture is then homogenised and cooled, with continued agitation, to 32–25° C. The active ingredients are added and agitation continued until the active ingredients are wetted and blended in. The mixture is once again homogenised and cooled until the cream thickens, around 30° C., before packaging.

EXAMPLE 2

A penciclovir/hydrocortisone composition according to the invention was prepared from the following components:

| oil phase | | |
|---|---|---|
| cetostearyl alcohol | 6.75 g | 6.75% |
| vaseline | 10.00 g | 10.0% |
| liquid paraffin | 5.65 g | 5.65% |
| isopropyl myristate | 15.00 g | 15.0% |
| aqueous phase | | |
| propylene glycol | 20.00 g | 20.0% |
| sodium lauryl sulphate | 0.80 g | 0.8% |
| poloxamer 188 | 1.00 g | 1.0% |
| aq. purif. | 34.8 g | 34.8% |
| active components | | |
| penciclovir | 5.00 g | 5.0% |
| hydrocortisone | 1.00 g | 1.0% |

The particle size of the hydrocortisone (Pharmacia & Upjohn micronised USP/EP/BP) was 100% <5 µm, geometric mean diameter 2 µm. The purified water is reverse osmosis treated. The penciclovir was micronised to mean diameter 5 µm.

The oil phase and aqueous phase components are added to respective mixing vessels, which are each heated to 70° C. under agitation. When the phases are at an identical temperature, the oil phase is poured onto the aqueous phase from above while continuing to agitate for 3–5 minutes at the highest possible speed which avoids drawing air into the mixture. The thus emulsified mixture is then homogenised and cooled, with continued agitation, to 32–25° C. The active ingredients are added and agitation continued until the active ingredients are wetted and blended in. The mixture is once again homogenised and cooled until the cream thickens, around 30° C., before packaging.

COMPARATIVE EXAMPLE 1

An acyclovir/hydrocortisone composition employing the prior art MAC carrier described and claimed in EP 44543 was prepared from the following components:

| oil phase | | |
|---|---|---|
| cetostearyl alcohol | 33.75 g | 6.75% |
| vaseline | 50.0 g | 10.0% |
| liquid paraffin | 28.25 g | 5.65% |
| aqueous phase | | |
| propylene glycol | 200.0 g | 40.0% |

-continued

| | | |
|---|---|---|
| sodium lauryl sulphate | 4.0 g | 0.8% |
| poloxamer 188 | 5.0 g | 1.0% |
| aq purif | 148.82 g | 29.8% |
| active components | | |
| acyclovir | 28.19 g | 5.0% |
| hydrocortisone | 5.02 g | 1.0% |

The ingedients were blended substantially as described in Example 1.

COMPARATIVE EXAMPLE 2

An acyclovir/hydrocortisone composition employing a low propylene glycol (PG) concentration (relative to the prior art MAC formulation) but without the isopropyl alkanoic ester (IPM) of the composition of the invention was prepared from the following components:

| | | |
|---|---|---|
| oil phase | | |
| cetostearyl alcohol | 6.75 g | 6.75% |
| vaseline | 10.00 g | 10.0% |
| liquid paraffin | 5.65 g | 5.65% |
| aqueous phase | | |
| propylene glycol | 25.00 g | 25% |
| sodium lauryl sulphate | 0.80 g | 0.8% |
| poloxamer 188 | 1.00 g | 1.0% |
| aq purif | 44.8 g | 44.8% |
| active components | | |
| acyclovir | 5.00 g | 5.0% |
| hydrocortisone | 1.00 g | 1.0% |

The ingredients were blended substantially as described in Example 1.

BIOLOGICAL EXAMPLE 1

Figure 1:
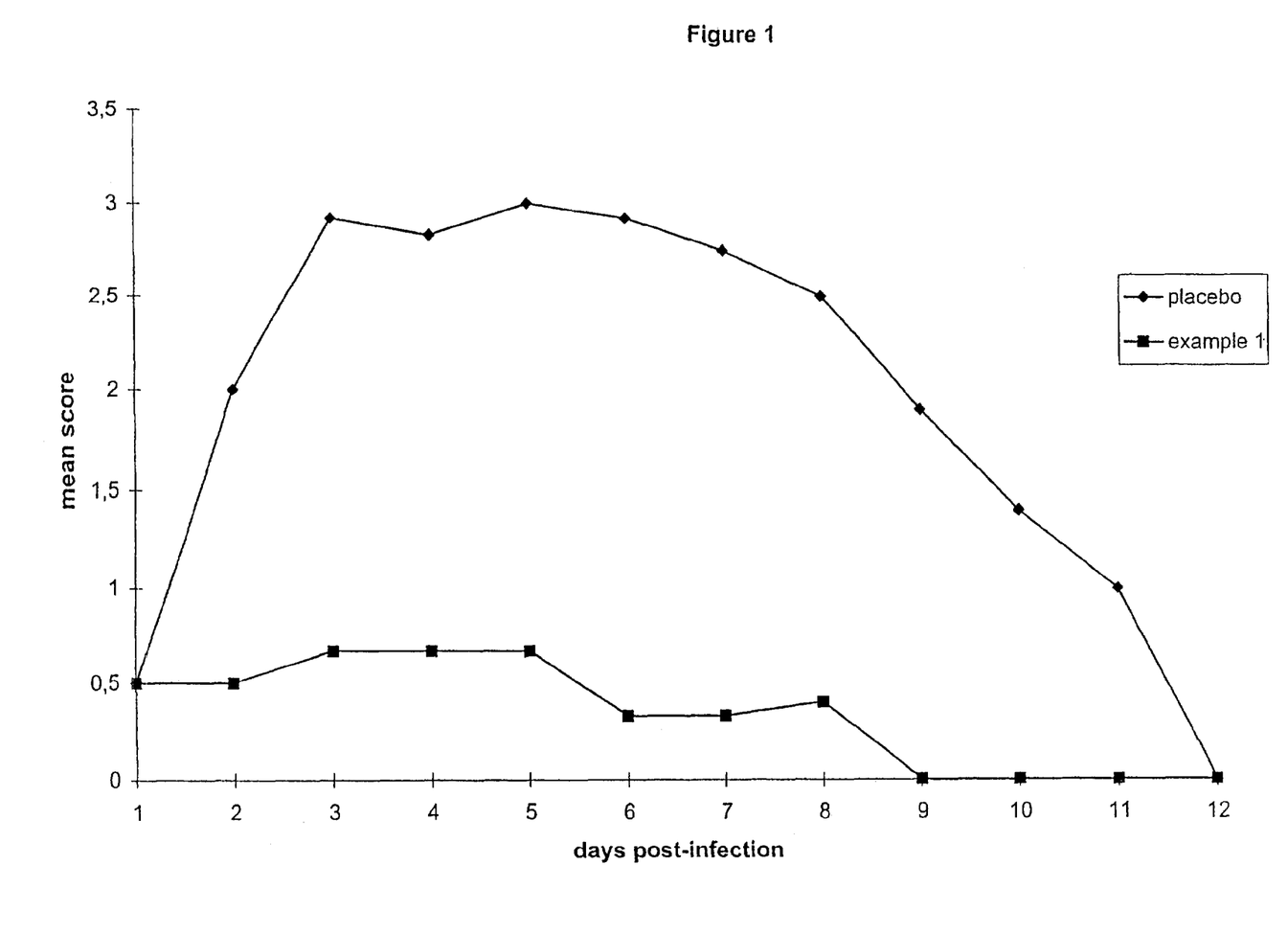
FIG. 1 is a plot of lesion score against time for herpes infected guinea pigs topically receiving a composition of the invention or a placebo.
Figure 2:
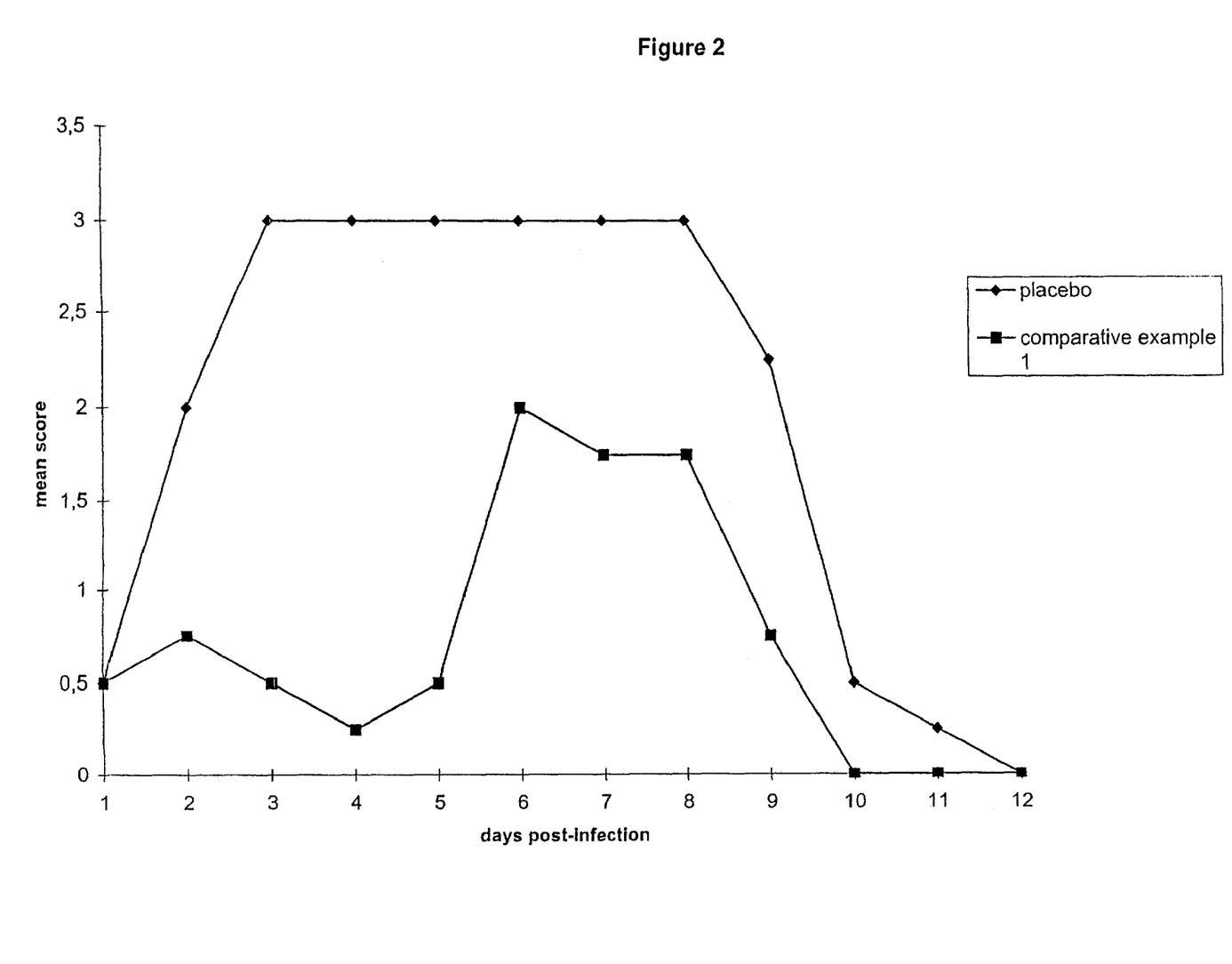
FIG. 2 is a plot of lesion score against time for herpes infected guinea pigs topically receiving a composition comprising a conventional carrier or a placebo.
Figure 3:
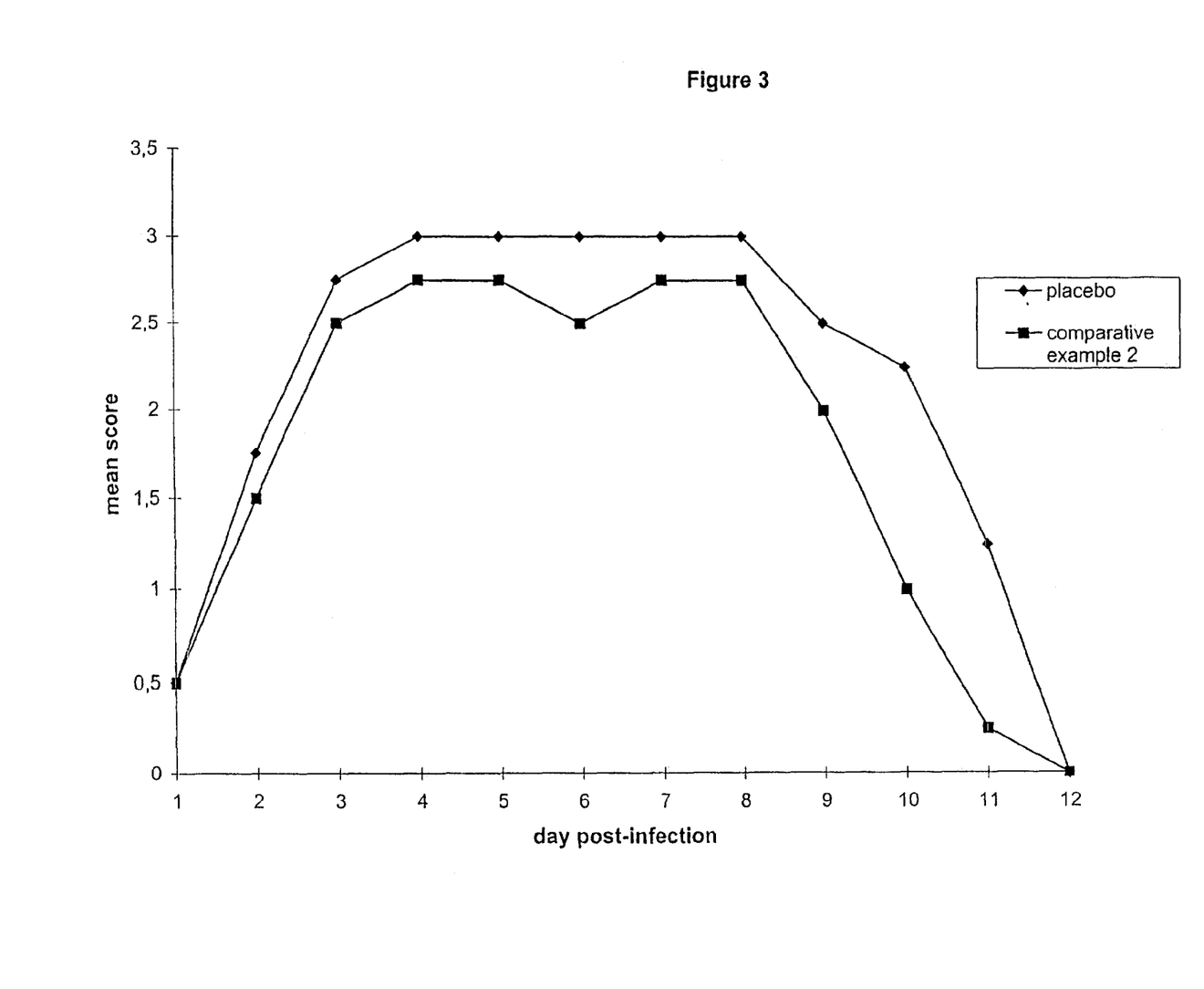
FIG. 3 is plot of lesion score against time for herpes infected guinea pigs topically receiving a composition falling outside the scope of the invention or a placebo.

Antiviral efficacy of compositions in accordance with the invention and comparative examples is assayed in a guinea pig model (Alenius et al, J. Inf. Dis. 145 569–573 (1982)). In summary, the model involves establishing a primary herpes simplex virus infection on depilated areas of the dorsal surface of guinea pigs. 24 hours after inoculation, the test and placebo compositions are smeared onto the incipient herpes lesions. This topical administration is repeated twice per day for 3 or 4 days. Lesion appearance is scored daily in a double blinded fashion and the scores from multiple animals averaged, wherein 0 represents no development of lesions,
1 represents a few scattered lesions,
2 represents several lesions, some confluent
3 represents maximum development of confluent lesions FIG. 1 shows the results from a composition in accordance with the invention (Example 1) in comparison to a placebo formulation (the MAC formulation analagous to Comparative Example 1, but without the active ingredients) which represents uninhibited viral growth. FIG. 2 shows a substantially prior art composition (Comparative Example 1—acyclovir & hydrocortisone in a MAC formulation) in comparison to the corresponding placebo. FIG. 3 shows a composition falling outside the scope of the invention (Comparative Example 2, low PG/IPM free) in comparison to the placebo.

Referring initially to the placebo formulations it will be apparent that in the absence of the combination of antiviral agent and glucocorticoid, severe lesions form within 3 days and remain unhealed for over 8 days.

A composition embodying the antiviral/glucocorticoid combination broadly in accordance with the abovementioned WO 96/24355 (Comparative Example 1) was freshly produced and comprised an antiviral nucleoside analogue and an antiinflammatory glucocorticoid in a conventional MAC formulation. This formulation displays a retarded development of serious lesions (days 1 to 5) and a somewhat diminished intensity of lesion (maximum score 2 at day 6). As suggested in WO 96/24355 such formulations are thus of utility in the treatment and prophylaxis of herpes infections. However, as described in Assay Example 1, this MAC formulation is not practical in a commercial context for combination regimens.

Turning now to Comparative Example 2 in FIG. 3, as would be predicted from the disclosure of the abovementioned EP 44543, WO 91/11187, EP 416 739 and WO 93/00905 directed to various aspects and applications of the MAC formulation, lowering the level of propylene glycol below the "at least 30 weight percent" advised by these patents and applications significantly reduces antiviral efficacy and results in a formulation which is only marginally better than the placebo. In particular, the lesion score is less that one half unit lower than the placebo with barely measurable decreases in time to lesion and time to heal.

In contrast, the compositions of the invention, as depicted in FIG. 1, show a significantly improved efficacy relative to both the placebo and the substantially prior art formulation of FIG. 2. In particular the lesion score remains at all times less than 1 and is below 0.5 at day 8. Clearly the combination of a reduced propylene glycol concentration in conjunction with the addition of the isopropyl alkanoic acid ester, isoropyl myristate, significantly aids antiviral and therapeutic efficacy of combination products comprising an antiviral and an antiinflammatory glucocorticoid.

Figure 6:
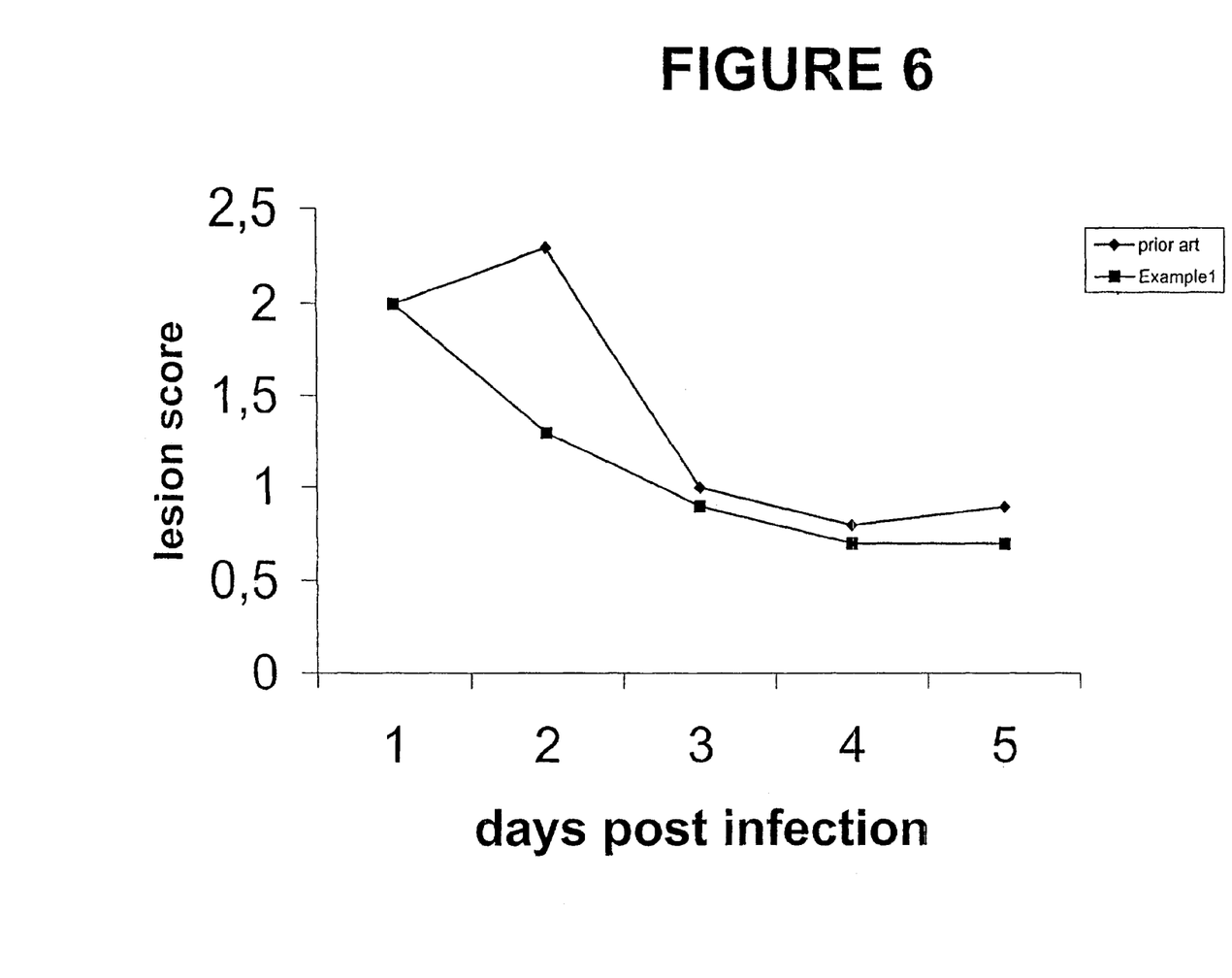
FIG. 6 is a plot of lesion score against time for herpes infected guinea pigs topically receiving a composition of the invention or a composition prepared according to WO 96/24355, example 3.

FIG. 6 depicts lesion score as a function of days in the guinea pig model broadly as described above but employing a slightly more pathogenic strain of herpes simplex type 1, from an experiment comparing the composition of the invention (Example 1) with a composition also comprising hydrocortisone and acyclovir but prepared according to Example 3 of our copending application WO96/24355. It will be apparent that both compositions provide good healing but the composition of the present invention has an improved performance as regards lesion severity in the early infection. When plotted to lesion disappearance, the area under the curve for the composition of the invention is approximately 10% less than that of the prior art formulation.

Figure 7:
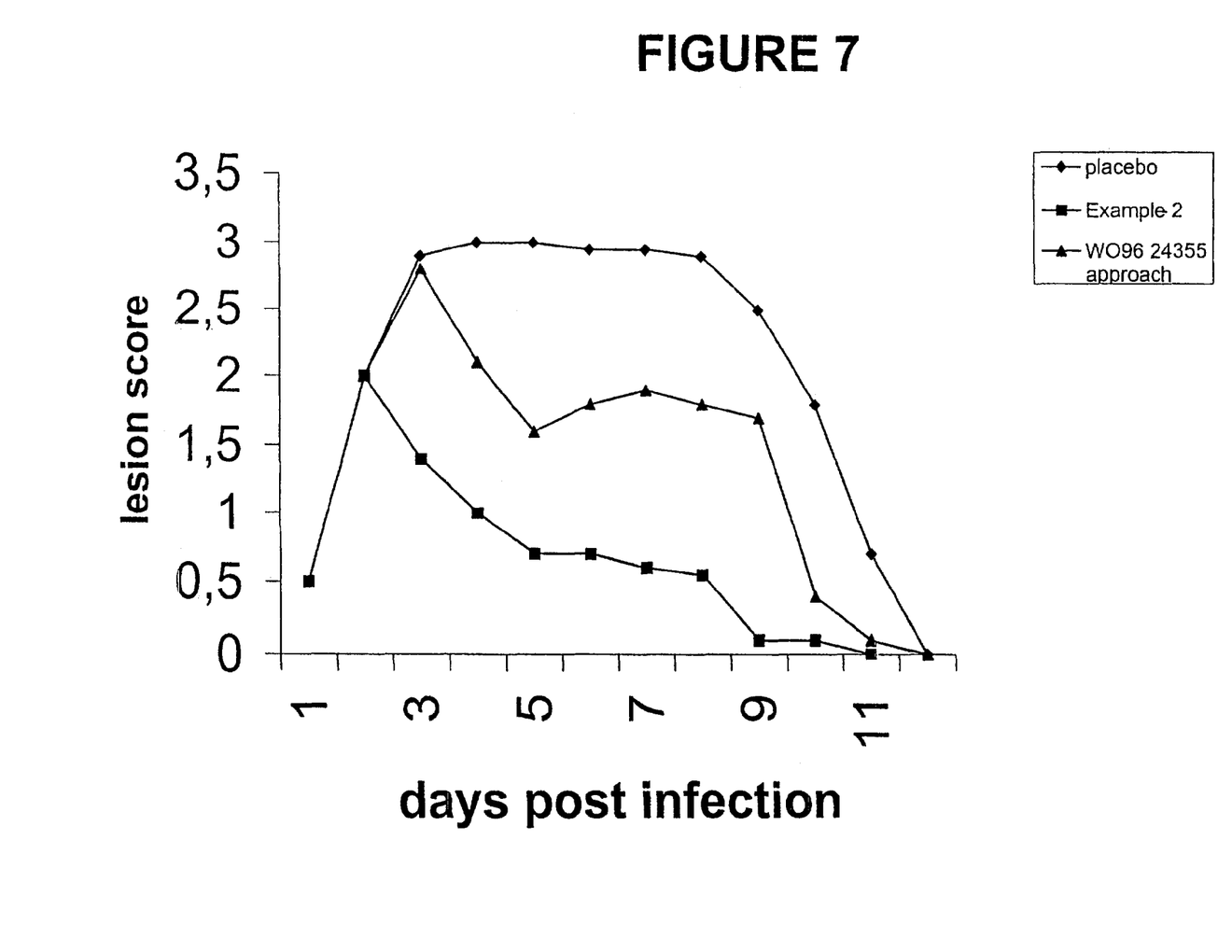
FIG. 7 is a plot of lesion score against time for herpes infected guinea pigs topically receiving an alternative composition of the invention or a composition prepared analogously to WO96/24355.

FIG. 7 depicts lesion score as a function of days in the guinea pig model described in relation to FIG. 6 from an experiment applying the cream of Example 2 containing an alternative antiviral penciclovir and the glucocorticoid hydrocortisone. For comparison, a cream was prepared analogously to the method described in our copending WO 96/24355 using commercially available Denavir® (penciclovir) (SmithKline Beecham) cream and ACO 1% hydrocortisone. The composition of the invention provides significantly less severe lesions score. The placebo animals treated with the corresponding active ingredient-free carrier are also depicted in FIG. 7.

ASSAY EXAMPLE 1

Figure 4:
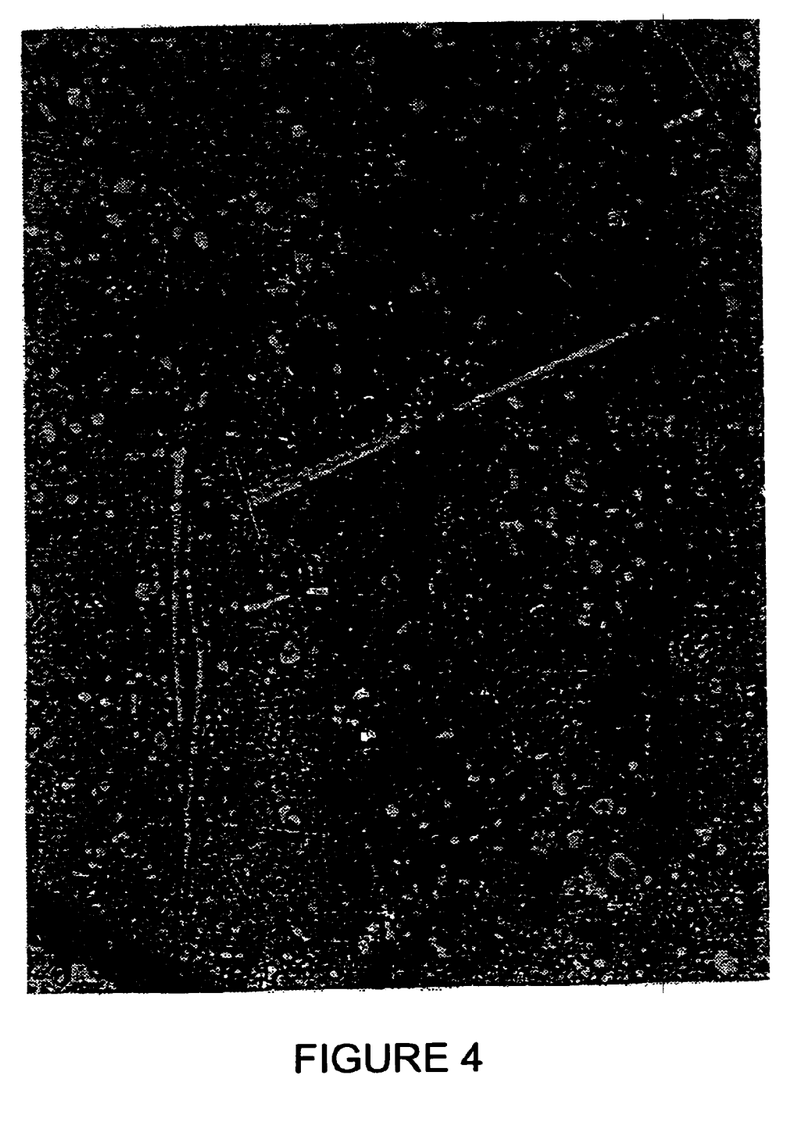
FIG. 4 is a micrograph showing crystal growth in a conventional formulation.
Figure 5:
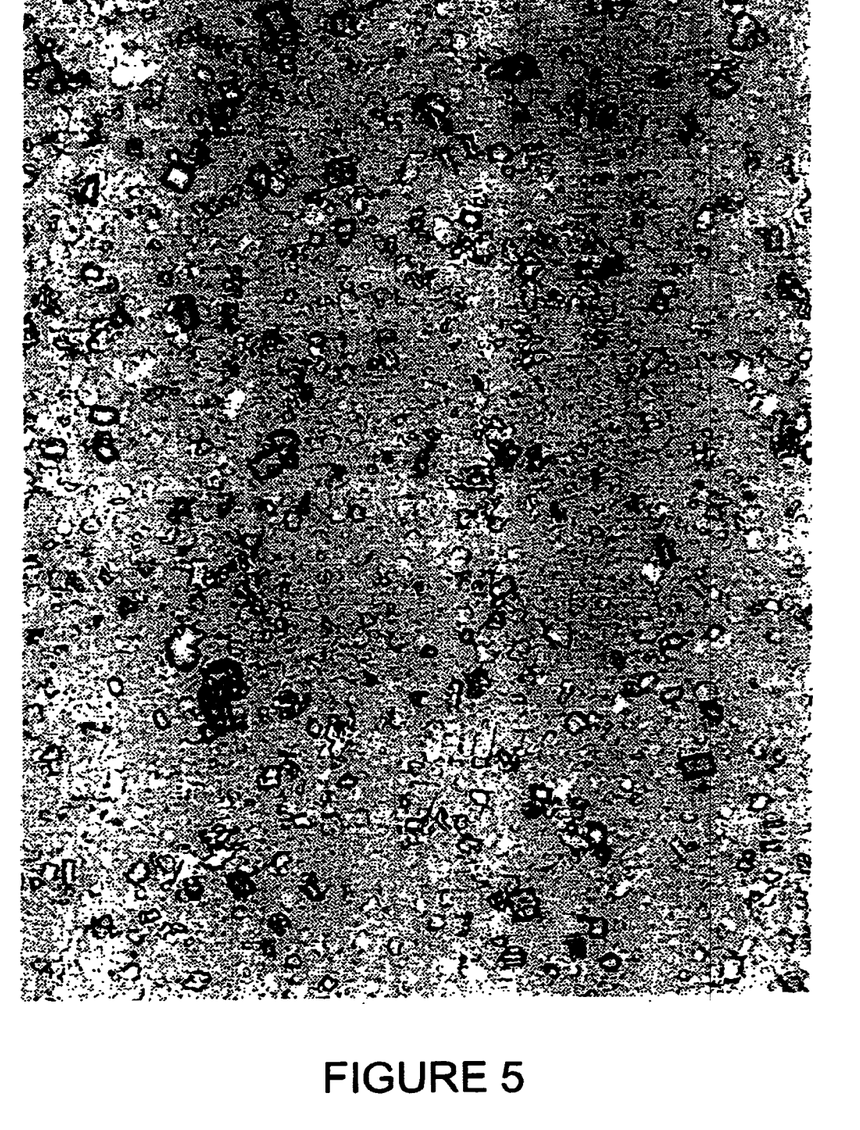
FIG. 5 is a micrograph showing the lack of crystal growth in a formulation of the invention.

FIGS. 4 and 5 are photomicrographs at 40× magnification of a composition reflecting a substantially prior art formulation (FIG. 4, Comparative Example 1) and a composition of the invention (FIG. 5, Example 1).

Referring inititially to FIG. 5, which depicts a composition of the invention after storage at 25° C. for six months, it will be apparent that the crystalline acyclovir and the globules of the oil phase are well dispersed in the aqueous phase. The appearance of this formulation after 6 month's storage is effectively identical to when the formulation was freshly prepared.

In contrast, FIG. 4 depicts a 40× magnification of a formulation comprising a glucocorticoid and an nucleoside analogue antiviral agent in a carrier which is formulated in accordance with prior art techniques, namely with around 40 weight % propylene glycol. When freshly prepared, this formulation was microscopically indistinguishable from the corresponding formulation in FIG. 5. However, after only 3 months and 3 weeks storage at 25° C., long needle like crystals have grown in this prior art formulation. Analysis shows that these needles comprise the hydrocortisone component of the formulation which has precipitated out of solution in the oil phase, leading to significantly suboptimal topically bioavailable amounts of this component in the formulation. Additionally it will also be apparent that the oil phase is less distinctly dispersed than in the micrograph of FIG. 5.

Although the invention has been illustrated with reference to certain proposed and concrete embodiments, exemplified by the antiviral agent acyclovir, the isopropyl alkanoic acid ester IPM etc, it will be appreciated that the invention is not limited by this disclosure and extends to the spirit and scope of the accompanying claims.

The invention claimed is:

1. A topical composition in the form of an oil in water emulsion comprising the lipophilic glucocorticoid hydrocortisone and a lipophobic acyclic nucleoside antiviral wherein the oil phase contains at least one member of the group consisting of mineral oil, alkanoic acids, fatty alcohols, straight chain mono alkyl esters, branched chain mono alkyl esters, straight chain dibasic alkyl esters and branched chain dibasic alkyl esters and contains said hydrocortisone; and said water phase contains 0.05–5% weight percent emulsifier and said acyclic nucleoside antiviral selected from the group consisting of acyclovir, penciclovir and 9-(4-hydroxy-2-(hydroxymethyl)butyl)guanine, the composition further comprising propylene glycol and isopropyl $C_{12}$–$C_{22}$ alkanoic acid ester selected from the group consisting of dodecanate, myristate, palmitate, stearate, eicosanate or behenoate esters, and mixtures thereof, wherein said hydrocortisone is 0.5 to 2 weight percent, said antiviral is 1 to 7 weight percent, said propylene glycol is 18 to 22 weight percent and said isopropyl $C_{12}$–$C_{22}$ alkanoic acid ester is 12 to 18 weight percent.

2. The composition according to claim 1 wherein the isopropyl alkanoic ester is isopropyl myristate.

3. The composition according to claim 1, wherein the nucleoside antiviral is acyclovir.

4. The composition according to claim 1, wherein the antiviral is acyclovir or penciclovir.

5. The composition according to claim 1, wherein acyclovir comprises 4–7 weight percent and hydrocortisone comprises 0.5–2 weight percent of the composition.

6. The composition according to claim 1, wherein penciclovir comprises 1–7 weight percent and hydrocortisone comprises 0.5–2 weight percent of the composition.

7. A method for the treatment of herpesvirus infections comprising the topical administration of a composition as defined in claim 1 to a subject in need thereof.

8. The composition according to claim 1, wherein the carrier comprises 20 weight percent propylene glycol.

9. The composition according to claim 1, wherein the carrier comprises 15 weight percent isopropyl alkanoic acid ester.

10. The composition according to claim 1, wherein the nucleoside antiviral comprises 4–7 weight percent of the composition.

11. The composition according to claim 1, which comprises 15 weight percent isopropyl myristate.

12. The composition according to claim 1, wherein said mineral oil is vaseline or liquid paraffin.

13. The composition according to claim 1, wherein said alkanoic acid is stearic acid.

14. The composition according to claim 1, wherein said fatty alcohol is cetostearyl alcohol.

15. The composition according to claim 1, wherein said emulsifier is poloxamer 188 or sodium lauryl sulphate.

16. The composition according to claim 1, wherein said oil phase is cetostearyl alcohol, vaseline and liquid paraffin.

17. The composition according to claim 1, wherein said emulsifier is poloxamer 188 and sodium lauryl sulphate.

18. The composition according to claim 1, wherein said antiviral is 5 weight percent acyclovir.

19. The composition according to claim 5, wherein said acyclovir is 5 weight percent and said hydrocortisone is 1 weight percent.

20. A method for the treatment of humans having or being at risk of developing herpesvirus infections comprising the topical administration of a composition as defined in claim 1.

* * * * *